US008588886B2

(12) United States Patent
de la Rama et al.

(10) Patent No.: US 8,588,886 B2
(45) Date of Patent: *Nov. 19, 2013

(54) BASKET CATHETER HAVING MULTIPLE ELECTRODES

(75) Inventors: Alan de la Rama, Cerritos, CA (US); Cary K. Hata, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,428

(22) Filed: Jul. 17, 2012

(65) Prior Publication Data

US 2013/0018246 A1 Jan. 17, 2013

Related U.S. Application Data

(63) Continuation of application No. 12/599,035, filed as application No. PCT/US2008/063204 on May 9, 2008, now Pat. No. 8,224,416.

(60) Provisional application No. 60/917,053, filed on May 9, 2007.

(51) Int. Cl.
*A61B 5/04* (2006.01)
*A61B 18/14* (2006.01)

(52) U.S. Cl.
USPC ............................................. 600/374; 606/41

(58) Field of Classification Search
USPC ...................... 600/374, 381; 606/41; 607/122
See application file for complete search history.

(56) References Cited

U.S. PATENT DOCUMENTS

| 4,940,064 | A | * | 7/1990 | Desai ............................ 607/122 |
| 5,345,936 | A | | 9/1994 | Pomeranz et al. |
| 5,411,025 | A | | 5/1995 | Webster, Jr. |
| 5,471,982 | A | | 12/1995 | Edwards et al. |
| 5,531,686 | A | * | 7/1996 | Lundquist et al. ......... 604/95.04 |
| 5,628,313 | A | | 5/1997 | Webster |
| 5,647,870 | A | | 7/1997 | Kordis et al. |
| 5,702,438 | A | * | 12/1997 | Avitall .......................... 607/122 |
| 5,730,128 | A | | 3/1998 | Pomeranz et al. |
| 5,855,552 | A | | 1/1999 | Houser et al. |
| 5,871,483 | A | | 2/1999 | Jackson et al. |
| 5,893,847 | A | | 4/1999 | Kordis |
| 5,904,680 | A | | 5/1999 | Kordis et al. |

(Continued)

FOREIGN PATENT DOCUMENTS

| WO | WO-96/34560 | 11/1996 |
| WO | WO-2006/058251 | 6/2006 |
| WO | WO-2008/141150 | 11/2008 |

*Primary Examiner* — Lee S Cohen
(74) *Attorney, Agent, or Firm* — Dykema Gossett PLLC (57) ABSTRACT

Embodiments of the present invention provide a catheter that comprises an elongated catheter body (16) and an electrode assembly (10) at the distal end of the catheter body. The electrode assembly comprises a plurality of spines (11), each of the spines having a proximal end connected to the distal end of the catheter and a distal end, the distal ends of the spines being connected at a spine tip junction (13). Each spine includes an elbow (20) having at least one discontinuity in stiffness at an intermediate position between the distal end and the proximal end thereof. The spines include a plurality of electrodes (12). The electrode assembly is collapsible to a collapsed arrangement to fit within a lumen of the elongated catheter body and expandable to an expanded arrangement with the elbows of the spines bending outwardly relative to the proximal and distal ends of the spines.

15 Claims, 9 Drawing Sheets

(56) References Cited

U.S. PATENT DOCUMENTS

| | | |
|---|---|---|
| 5,925,038 A | 7/1999 | Panescu et al. |
| 5,928,228 A | 7/1999 | Kordis et al. |
| 6,016,437 A | 1/2000 | Tu et al. |
| 6,119,030 A | 9/2000 | Morency |
| 6,216,043 B1 | 4/2001 | Swanson et al. |
| 6,741,878 B2 | 5/2004 | Fuimaono et al. |
| 6,748,255 B2 | 6/2004 | Fuimaono et al. |
| 6,973,340 B2 | 12/2005 | Fuimaono et al. |
| 7,149,563 B2 | 12/2006 | Fuimaono et al. |
| 7,245,955 B2 * | 7/2007 | Rashidi ......................... 600/374 |
| 7,257,434 B2 | 8/2007 | Fuimaono et al. |
| 7,269,453 B2 * | 9/2007 | Mogul ......................... 600/374 |
| 7,291,146 B2 | 11/2007 | Steinke et al. |
| 7,429,261 B2 * | 9/2008 | Kunis et al. ..................... 606/41 |
| 7,474,909 B2 | 1/2009 | Phan et al. |
| 7,615,049 B2 | 11/2009 | West et al. |
| 8,224,416 B2 * | 7/2012 | de la Rama et al. .......... 600/374 |
| 8,380,275 B2 | 2/2013 | Kim et al. |
| 2002/0138075 A1 | 9/2002 | Edwards et al. |
| 2003/0114739 A1 | 6/2003 | Fuimaono et al. |
| 2004/0133091 A1 | 7/2004 | Fuimaono et al. |
| 2006/0009690 A1 | 1/2006 | Fuimaono et al. |
| 2007/0276212 A1 | 11/2007 | Fuimaono et al. |
| 2009/0182325 A1 * | 7/2009 | Werneth et al. ................. 606/41 |
| 2011/0213231 A1 | 9/2011 | Hall et al. |

\* cited by examiner

BASKET CATHETER HAVING MULTIPLE ELECTRODES

CROSS-REFERENCE TO RELATED APPLICATIONS

This application is a continuation of U.S. application Ser. No. 12/599,035, filed on Nov. 5, 2009 (the '035 application), now U.S. Pat. No. 8,224,416 issued on 17 Jul. 2012, which is the national stage of international application no. PCT/US2008/063204, with an international filing date of 9 May 2008 (the '204 application), which claims priority to U.S. provisional application No. 60/917,053, filed on 9 May 2007 (the '053 application). The '035 application, the '204 application, and the '053 application are each hereby incorporated by reference as though fully set forth herein.

BACKGROUND OF THE INVENTION a. Field of the Invention

The present invention pertains generally to catheters and electrode assemblies. More particularly, the present invention is directed toward mapping catheters including high density mapping catheters, and ablation catheters.

b. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

By mapping the electrical activities using mapping electrodes of a catheter, one can detect ectopic sites of electrical activation or other electrical activation pathways that contribute to cardiac disorders. This type of information is very valuable and allows a cardiologist to locate and treat dysfunctional cardiac tissues. Ablation electrodes can be provided on a catheter for ablating cardiac tissue. Ablation is considered a field within electrophysiology and is important because it obviates the need for more invasive and risky surgical treatments such as open heart surgery.

Typically, the electrode catheter is inserted into a major vein or artery, and then guided into the heart chamber of concern. Due to the unpredictability of the interior size and shape of an individual's heart and the location of the area of concern, the ability to control the exact position and orientation of the catheter is essential and critical to the effectiveness of the ablation treatment by electrode catheter.

Such electrophysiological ablation and mapping catheters typically have an elongated flexible body with a distal end that carries one or more electrodes that are used to map or collect electrical information about electrical activities in the heart. Typically, the distal end is steerable to provide the user the ability to adequately guide and position the catheter to the desired location. Some types of electrode ablation and mapping catheters (see, e.g., U.S. Pat. No. 7,027,851, which is hereby incorporated, by reference in its entirety) use multiple electrode arms or spines to allow multiple measurements to be taken at once, thereby reducing the time it takes to map the heart. Although such types of electrode ablation and mapping catheters make mapping more efficient, they suffer from the lack of control over the individual electrode spines or arms. In addition, because of the unpredictable and often irregular shapes and sizes of the inner-heart, such uncontrollable independent configuration of electrode spines or arms often lead to unreliable mapping and ablation, because the user cannot adequately predict or control where a particular electrode spine or arm will be positioned relative to another electrode spine or arm. Accordingly, the need exists for an improved catheter that can more effectively control and position multiple electrode members and increase location predictability of electrode members, while being steerable and deflectable.

BRIEF SUMMARY OF THE INVENTION

Embodiments of the present invention provide a catheter including an electrode assembly or basket having an array of electrodes. In specific embodiments, the electrode assembly is particularly useful for mapping electrical activity at multiple locations within the heart. The electrode assembly includes a plurality of spines each having at least one discontinuity in stiffness at an elbow region between its proximal end and its distal end to allow the spines to bend outwardly at the elbow region as the electrode assembly move from a collapsed arrangement to an expanded arrangement. In some cases, the distal segment between the elbow and the distal end of each spine remains generally linear. An adjusting member may be provided to move the electrode assembly between the collapsed arrangement and the expanded arrangement. Optionally, a transverse spine or link connects the elbows of a plurality of longitudinal spines.

In accordance with an aspect of the present invention, a catheter comprises an elongated catheter body having a proximal end and a distal end, and at least one lumen therethrough in a longitudinal direction of the elongated catheter body; and an electrode assembly at the distal end of the catheter body. The electrode assembly comprises a plurality of spines, each of the spines having a proximal end connected to the distal end of the catheter and a distal end, the distal ends of the spines being connected at a spine tip junction. Each spine includes an elbow having at least one discontinuity in stiffness at an intermediate position between the distal end and the proximal end thereof. The spines include a plurality of electrodes. The electrode assembly is collapsible to a collapsed arrangement to fit within a lumen of the elongated catheter body and is expandable to an expanded arrangement with the elbows of the spines bending outwardly relative to the proximal and distal ends of the spines. The elbows of the spines move radially outwardly from the collapsed arrangement to the expanded arrangement.

In some embodiments, the elbow of each spine has at least one discontinuity in stiffness resulting from one or more of a change in material, a change in cross-sectional arrangement, and a change in cross-sectional area. Each spine has electrodes only between the elbow and the distal end thereof or only between the elbow and the proximal end thereof. A tilting mechanism is used to tilt the electrode assembly with respect to the elongated catheter body. A bending mechanism is provided to bend the elongated catheter body. The spines include mapping electrodes, and the spine tip junction includes an ablation electrode. The spines may include mapping electrodes, and the electrodes in one spine are spaced differently from the electrodes in another spine. At least one of the spines includes a shape memory material that biases the spine toward the expanded arrangement.

In specific embodiments, a transverse link connects the elbows of at least some of the spines, wherein the transverse link is collapsible to fit within the lumen of the elongated catheter body. The transverse link includes a shape memory material that biases the spines toward the expanded arrangement. At least one spine has an ablation electrode disposed at the elbow thereof. An adjusting member has a distal end connected to the spine tip junction and a proximal end which is movable in the longitudinal direction of the elongated catheter body, wherein movement of the adjusting member changes the shape of the electrode assembly.

In accordance with another aspect of the invention, a catheter comprises an elongated catheter body having a proximal end and a distal end, and at least one lumen therethrough in a longitudinal direction of the elongated catheter body; and an electrode assembly at the distal end of the catheter body. The electrode assembly comprises a plurality of spines, each of the spines having a proximal end connected to the distal end of the catheter and a distal end, the distal ends of the spines being connected at a spine tip junction. Each spine includes an elbow having at least one discontinuity in stiffness at an intermediate position between the distal end and the proximal end thereof. The spines include a plurality of electrodes. An adjusting member has a distal end connected to the spine tip junction and a proximal end which is movable in the longitudinal direction of the elongated catheter body. Movement of the adjusting member changes the shape of the electrode assembly between a collapsed arrangement in which the electrode assembly is collapsed to fit within a lumen of the elongated catheter body and different expanded arrangements with the elbows of the spines bending outwardly relative to the proximal and distal ends of the spines. The elbows of the spines move radially outwardly from the collapsed arrangement to the expanded arrangement.

In accordance with another aspect of the present invention, a catheter comprises an elongated catheter body having a proximal end and a distal end, and at least one lumen therethrough in a longitudinal direction of the elongated catheter body; and an electrode assembly at the distal end of the catheter body. The electrode assembly comprises a plurality of spines including multiple longitudinal spines and a transverse spine, each of the longitudinal spines having a proximal end connected to the distal end of the catheter and a distal end, the distal ends of the longitudinal spines being connected at a spine tip junction. Each longitudinal spine includes an elbow having at least one discontinuity in stiffness at an intermediate position between the distal end and the proximal end thereof. The transverse spine connects the elbows of at least some of the longitudinal spines. The spines include a plurality of electrodes. The electrode assembly is collapsible to a collapsed arrangement to fit within a lumen of the elongated catheter body and is expandable to an expanded arrangement with the elbows of the longitudinal spines bending outwardly relative to the proximal and distal ends of the longitudinal spines. The elbows of the spines move radially outwardly from the collapsed arrangement to the expanded arrangement.

In some embodiments, the transverse spine forms a loop around the elbows of the longitudinal spines. The spines include electrodes only along the loop. The transverse spine includes a shape memory material that biases the spines toward the expanded arrangement.

The foregoing and other aspects, features, details, utilities, and advantages of the present invention will be apparent from reading the following description and claims, and from reviewing the accompanying drawings.

DETAILED DESCRIPTION OF EXEMPLARY EMBODIMENTS

Figure 1:
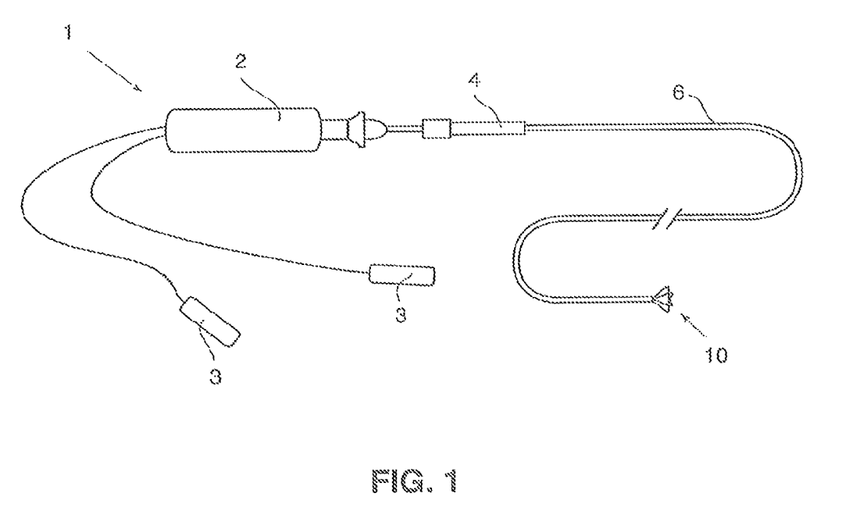
FIG. 1 is a perspective view of a catheter system according to an embodiment of the present invention.

FIG. 1 is a perspective view of a catheter system 1 according to an embodiment of the present invention. The catheter system 1 includes a handle 2 and connectors 3 disposed proximal to the handle 2 for making electrical connections to an electronic mapping system or the like (not shown). The handle 2 can have a uni-directional design, a bi-directional design, a double bi-directional design, or any other suitable design. The catheter system 1 also has a delivery sheath intro 4 located distal to the handle 2 that a surgeon may use to deliver a sheath 6 into the body of a patient. The sheath 6 extends from the delivery sheath intro 4. Further, an electrode assembly or basket 10 protrudes from the distal end of the sheath 6. As those of ordinary skill in the art will recognize, the handle 2, the delivery sheath intro 4, and electronic connectors 3 may readily be modified as dictated by the aesthetic or functional needs of particular applications.

Figure 2A:
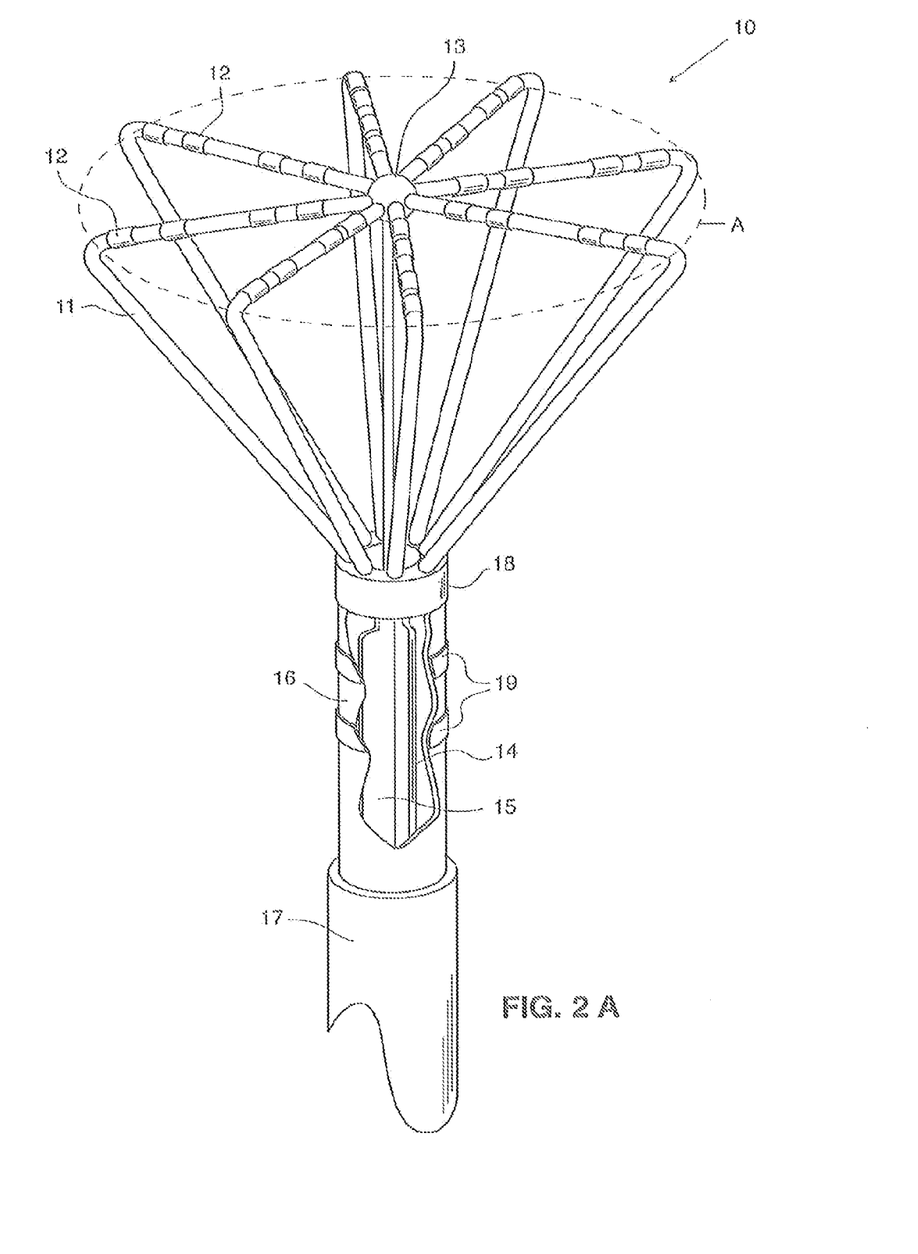
FIG. 2A is a perspective view of a catheter showing an electrode assembly or basket in an expanded profile.
Figure 2B:
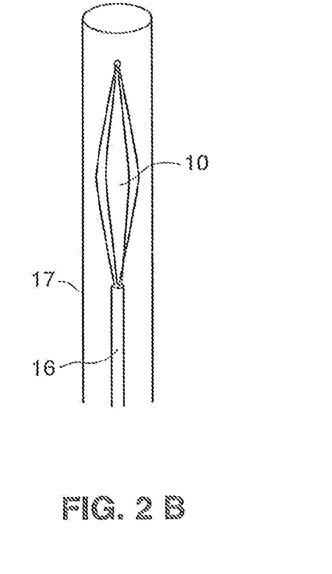
FIG. 2B is a perspective view of the electrode assembly in a collapsed profile inside a sheath.

FIGS. 2A and 2B illustrate the electrode assembly 10 in greater details. FIG. 2A shows the electrode assembly 10 in an expanded profile, while FIG. 2B shows the electrode assembly 10 in a collapsed profile inside a sheath 17. The electrode assembly 10 may be collapsed by a force to the collapsed profile and, upon removal of the force, returns to the expanded profile. This may be achieved by using a shape memory material or some other biasing mechanism. The electrode assembly 10 shown has eight spines 11. Each of the spines 11 has a distal and a proximal end. The spines are deflectable elongated pieces that carry electrodes 12 along a length of the spines 11. In this embodiment, a plurality of electrodes 12 are disposed between the elbow regions 20 (as discussed below in connection with FIGS. 3A-3D) and the distal ends of the spines 11. When the electrode assembly 10 is in the expanded profile, according to this particular embodiment, the electrodes 12 on the spines 11 form an array of electrodes distributed over a substantially flat surface within an area encircled by dashed line A. The electrode assembly 10 has a generally cone shape in the expanded profile. Of course, the array of electrodes 12 need not be distributed over a substantially flat surface but may take on a nonplanar surface profile in the expanded state in other embodiments depending on the application of the electrode assembly. In specific embodiments, the spines 11 include mapping electrodes 12 that are spaced differently among the different spines 11 so as to provide orientation information for the mapping. In other embodiments, an ablation electrode is provided at one or more of the elbows 20 of the spines 11.

Figure 5:
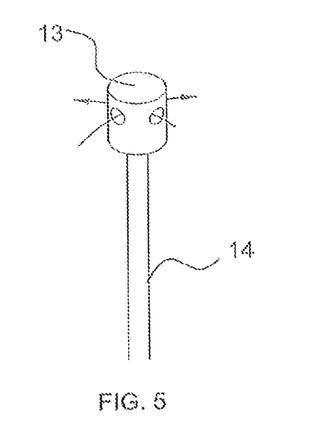
FIG. 5 is a perspective view of the tip junction of the electrode assembly of a catheter according to an embodiment of the invention.

The distal ends of the spines 11 are connected at a tip junction 13 (see FIG. 5). The electrode assembly 10 is coupled at its proximal end to a distal end of a longitudinal shaft 16, and the shaft 16 is slidably received within a longitudinal lumen of the sheath 17. In FIG. 2B, the collapsible electrode assembly 10 is in a collapsed profile and is slidably received within the longitudinal lumen of the sheath 17. During delivery of the catheter into the target site within a patient's body, the electrode assembly 10 remains collapsed as shown in FIG. 2B. The electrode assembly 10 expands, as shown in FIG. 2A, when it is pushed through the distal end of the sheath 17 at the target site. The elbows 20 of the spines 11 move radially outwardly and the spine tip junction 13 move closer to the distal end of the catheter shaft 16 as the electrode assembly 10 moves from the collapsed profile to the expanded profile. The electrode assembly 10 is preferably biased from the collapsed state toward the expanded state when the force applied to move it to the collapsed state is removed. As discussed in more detail below, this can be achieved by using shape memory materials or the like.

The tip junction 13 may be a block with a plurality of transverse through holes, as seen in FIG. 5. The transverse through holes receive spines 11. The spines 11 can be fastened to the tip junction 13 by adhesives, welding or other suitable means. The tip junction 13 is connected to the distal end of an adjusting member 14 which may be in the form of a control wire. The adjusting member 14 extends into the shaft 16 and is slidably received within the shaft. The proximal end of the adjusting member 14 is coupled to a user-actuated controller such that movement of the adjusting member 14 in a proximal direction will also move the tip junction 13 in the proximal direction, which in turn causes the electrode assembly 10 to move toward or away from the expanded profile as shown in FIG. 2A and FIG. 3A.

Optionally, the tip junction 13 can be an electrode for mapping and/or ablating. In such an embodiment, the tip junction 13 is electrically connected to a power source and can selectively apply energy, or collect electrical data, or both.

Figure 3A:
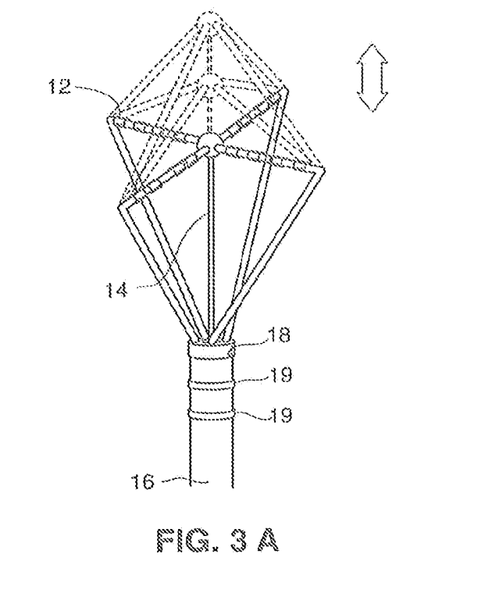
FIGS. 3A-3D illustrate the electrode assembly having spines formed of generally linear spine segments at different stages of expansion from the collapsed profile to the expanded profile, and having electrodes disposed between the elbows and the distal ends of the spines, according to an embodiment of the invention.

In the embodiment of FIG. 3A, the electrode assembly 10 has four spines 11. The dashed lines illustrate different stages of collapse of the electrode assembly 10 from the expanded profile by selectively and slidably move the adjusting member 14. In this embodiment, the proximal ends of spines 11 are connected to a base socket support member 18 at the distal end of the shaft 16. The base socket support member 18 provides structural support to secure the plurality of spines 11 to the shaft 16, while allowing pivotal movement of individual spines 11 during expansion and during collapse of the electrode assembly 10.

As seen in FIG. 2A, a flat wire 15 is provided in the shaft 16 for bi-directional deflection of the shaft 16. In the embodiment shown, the flat wire 15 does not extend through the distal end of the shaft 16, and is contained within shaft 16. Additionally and optionally, shaft electrodes 19 are disposed near the distal end of the shaft 16 for visualization and/or mapping purposes as used, for instance, in the EnSite™ system available from St. Jude Medical.

Figure 3B:
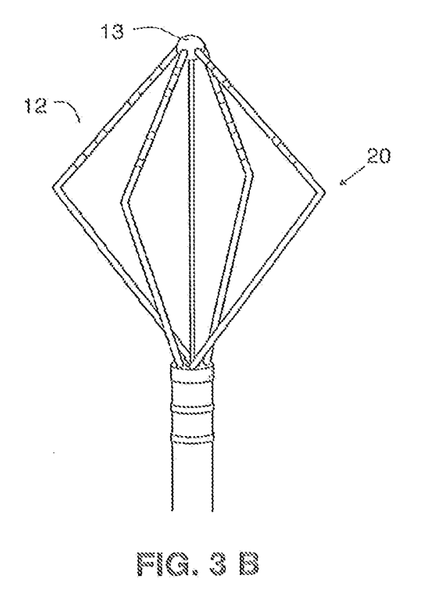
Figure 3C:
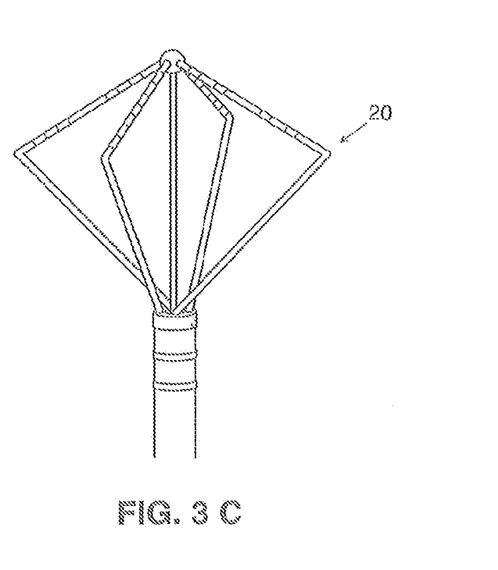
Figure 3D:
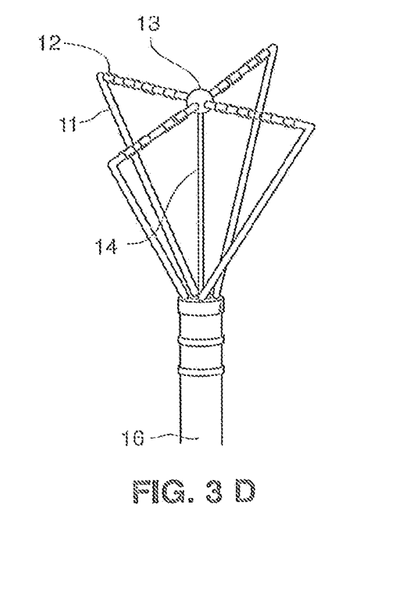

FIGS. 3B-3D illustrate the electrode assembly 10 at different stages of collapse or expansion as the adjusting member 14 moves forward and backward along the longitudinal direction of the shaft 16. The electrode assembly 10 has spines 11 formed of generally linear spine segments. There are two spine segments separated by an elbow region 20 in an intermediate position between the distal end and the proximal end of the embodiment shown. A distal segment extends from the elbow 20 to the distal end connected to the tip junction 13. A proximal segment extends from the elbow 20 to the proximal end connected to the support member 18. In this embodiment, electrodes are disposed between the elbows 20 and the distal ends of the spines 11. The elbow 20 bends outwardly relative to the proximal end and the distal end of the spine 11. The elbow 20 has at least one discontinuity in stiffness that allows it to bend. The at least one discontinuity may result from one or more of a change in material, a change in cross sectional arrangement (e.g., shape), and a change in cross-sectional area. In a specific embodiment, the cross section of the spine 11 changes from the proximal segment to a less stiff cross section at the elbow 20 (by reducing the area and/or the shape of the cross section) and then changes back to the same cross section in the distal segment as in the proximal segment. The elbow 20 may be located in the mid portion of each spine 11. The location of the elbow 20 affects the size of the area A of the electrode array in this embodiment (see circle A in dash line in FIG. 2A), and defines the shape of the electrode assembly or basket 10. The elbow region 20 may be selected for each spine 11 to define a desired shape and size of area A for the electrode array, for instance, based on the type and shape of the target tissue.

Figure 3E:
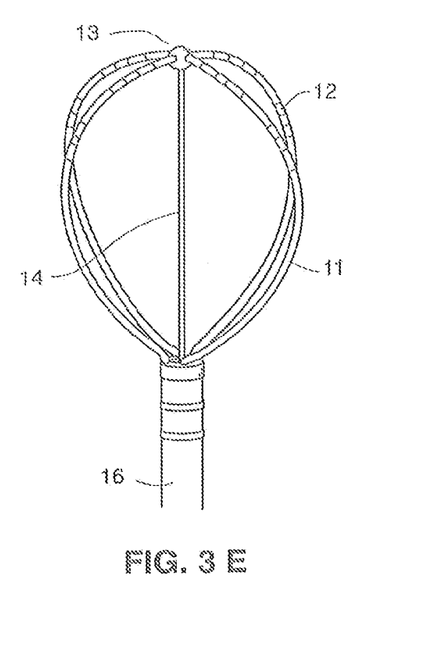
FIGS. 3E-3G illustrate an electrode assembly having arcuate shape spines according to another embodiment of the invention.
Figure 3F:
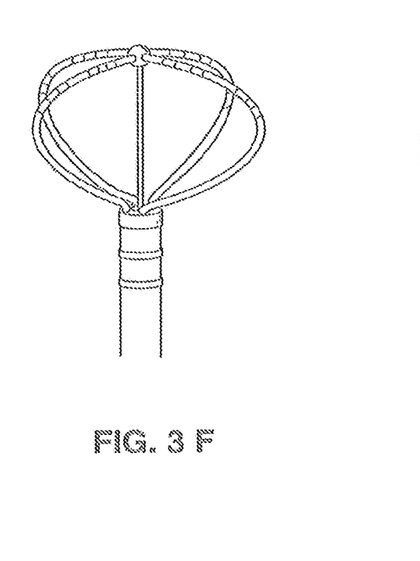
Figure 3G:
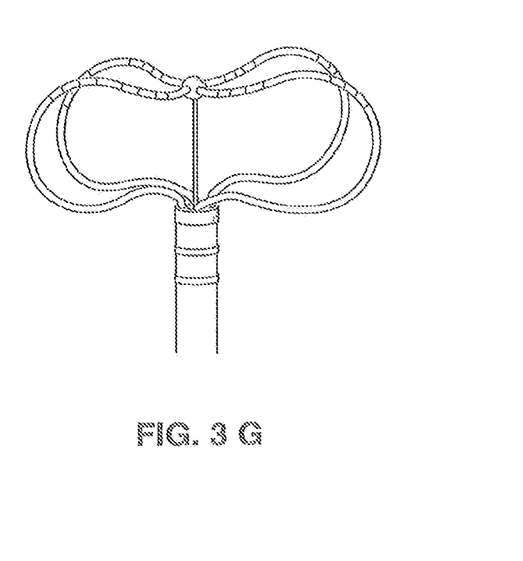

Other configurations of the electrode assembly or basket 10 are possible. For example, FIGS. 3E-3G show spines 11 without elbow regions, and the spines 11 bend in an arcuate manner in response to movement of the adjusting member 14. As a result, a generally oval or spherical shape is formed instead of a conical or diamond shape.

FIGS. 4A-4D illustrate various configurations of internal support members of the spines 11 that define the deflection characteristics of the spines 11 according to different embodiments. In these embodiments, each spine 11 has an internal support member 21 embedded in a shell typically having a circular cylindrical shape. The internal support member 21 provides structural integrity and defines elbow regions for spine deflection. Each support member 21 shown supports two opposing spines 11 that are joined at the tip junction 13. Referring to the four diamond-shaped internal support members 21 in FIGS. 4A-4D, the topmost point 22 of the diamond is where tip junction 13 is located. The two terminal ends 23 of the internal support members are secured to base socket support member 18. The distal segment 24 is disposed between the elbow region 25 and the topmost point 22, and the proximal segment 26 is disposed between the elbow region 25 and the terminal ends 23. The topmost point 22 has a bend that can be achieved by a discontinuity (similar to the elbow 25) or by use of a shape memory material. An optional bent knee 29 is provided near each terminal end 23. The elbows 25 are characterized by a change or discontinuity in cross-sectional shape and area. Unlike a hinge, the elbow 25 in these embodiments is typically not a point but a region that includes the discontinuity in stiffness. In other embodiments, the elbow 25 will appear more like a point if the discontinuity is formed by a hinge or hinge-like mechanism.

Figure 4A:
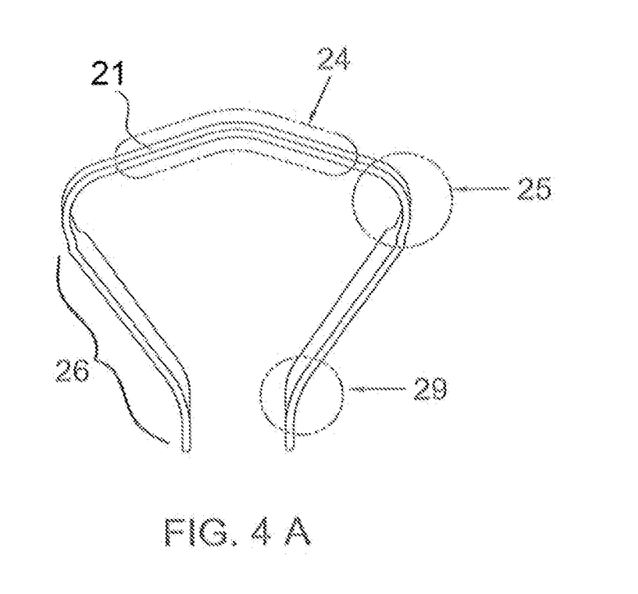
FIGS. 4A-4D illustrate various configurations of internal support members of spines according to different embodiments.

More specifically, FIG. 4A shows an internal support member 21 that has a flat, rectangular cross-sectional shape throughout. The proximal segment 26 is wider than the distal segment 24 (and has a larger cross-sectional area), and is thus structurally stronger against deflection. In some embodiments, the proximal segments 26 may be sufficiently sturdy so that when the array of electrodes are pressed against tissues with ridges or irregularities on the surface of the tissue, the proximal segments 26 do not bend out of shape but support and maintain the contact between the array of electrodes and the tissue surface. Such a design maintains the integrity of the electrode assembly 10 such that its shape is not changed when pressed upon ridges on the tissue surface.

In other embodiments, the distal segments 24 are relatively stiffer than the rest of the support member 21, so that at least when the electrode assembly 10 is in an expanded profile, the distal segments 24 remain substantially straight. In yet other embodiments, the support member 21 may have a generally uniform cross section except at the elbows 25 (and optionally the topmost point 22) where the cross section is reduced in size or otherwise shaped to provide a discontinuity in stiffness or weaker area to facilitate deflection. As mentioned, a hinge mechanism or the like may also be employed at the discontinuity.

Figure 4B:
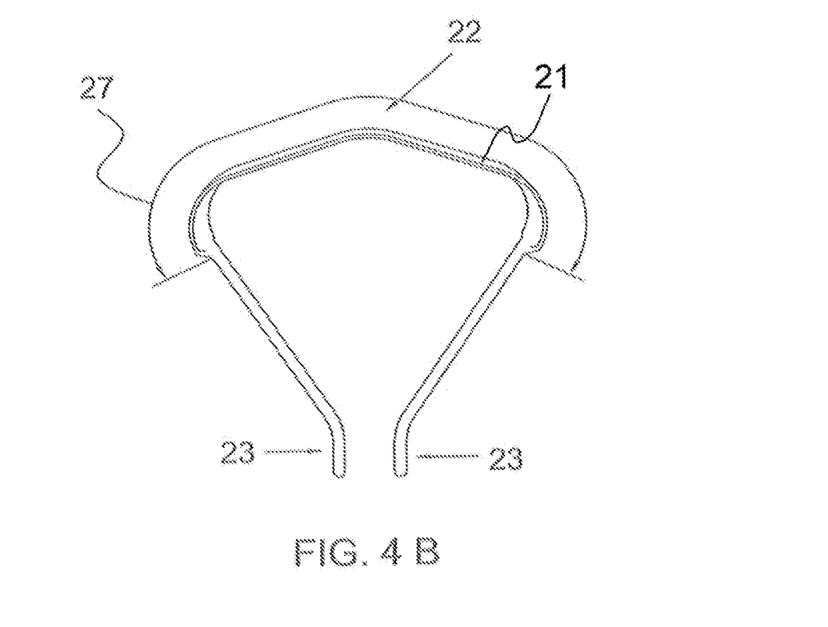

In FIG. 4B, the internal support member 21 has a flat, rectangular cross-sectional shape in the distal segments 24 and in the elbow region 25 only. The distal segments 24 and the elbow region 25 can be referred to as a tapered section 27, which is generally of a thinner and flatter profile than proximal segments 26. The proximal segments 26 in FIG. 4B have a generally round cross-sectional shape, and are sized to be structurally stiffer against bending than the elbow region 25.

Figure 4C:
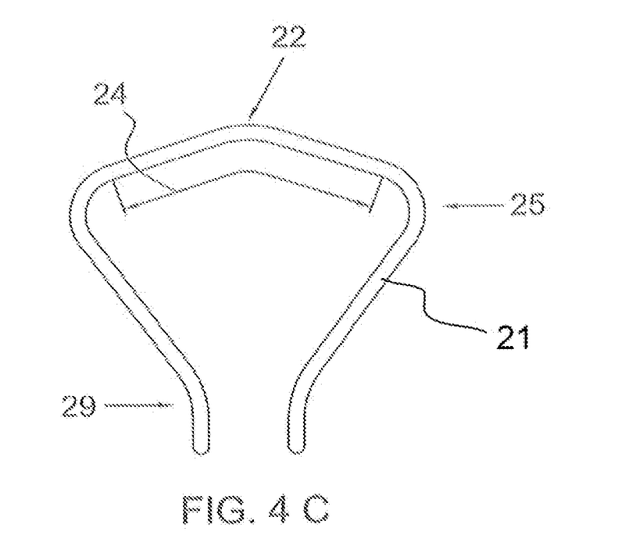

In FIG. 4C, the internal support member 21 has a generally round cross-sectional shape throughout. The proximal segments 26 are larger in diameter than the distal segments 24 and the elbow region 25. Alternatively, the entire internal support member can have a round cross-sectional shape, except at the angled points (elbow region 25 and topmost point 22) wherein a flat, rectangular cross-sectional shape or the like is provided to enhance pivotal bending at those angle points.

Figure 4D:
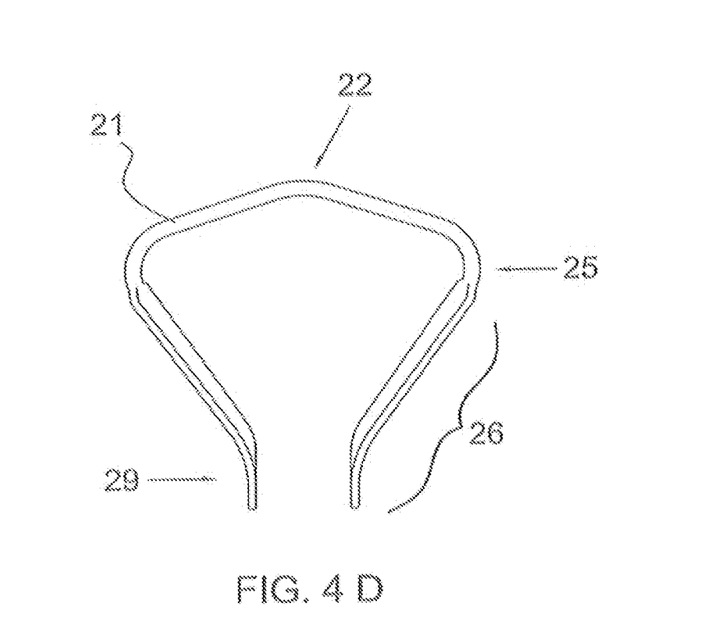

In FIG. 4D, the internal support member 21 has a generally round cross-sectional shape in the distal segments 24 and the elbow region 25. The proximal segments 26 have a generally flat, rectangular cross-sectional shape that is configured to be structurally stiffer than the distal segment 24 and the elbow region 25.

Although specific shapes of internal support member 21, spines 11, tip junction 13, and base socket support member 18 are disclosed for the collapsible electrode assembly 10, one of ordinary skill in the art will recognize there are other ways to build a collapsible assembly. For example, instead of providing a unitary internal support member 21 that passes through a tip junction 13 to form opposing spines 11, one can use two opposing internal support members 21 for the two opposing spines 11 that are connected at the tip junction 13 by welding or the like. In addition, the cross-sectional shapes and configuration of the internal support members 21 described may readily be modified as dictated by the functional needs of providing sufficient structure integrity, allowing deflection in the elbow region 25 and other designated regions, and providing sufficient stiffness in the distal segments 24 to ensure that, the distal segments 24 remain substantially straight during ablation/mapping of tissue. Different thicknesses can also be utilized in different areas along the support member 21 to achieve the desired deflection. For example, the elbow region 25 and the topmost point 22 can be thinner or otherwise made structurally more tenuous than other parts of the support member 21, such that the desired bending occurs at the elbow regions 25 and the topmost point 22, and not in other parts of the support member 21.

In specific embodiments, the spines 11 are generally evenly spaced in the electrode assembly or basket 10 to form a stable and sturdy structure that allows the electrode array to maintain its shape during use. This is particularly helpful if the electrode array is adapted to contact body tissue having ridges or an otherwise uneven surface (e.g., cardiac tissue of the heart). One contemplated way of providing sufficiently sturdy spines 11 is to use flat internal support members 21 that only bend bi-directionally. In this way, the electrode assembly 10 can expand and collapse, but the spines 11 will not move from side to side. Another contemplated design is to have internal support members 21 made of sufficiently stiff material such that side-to-side movement is minimized. Optionally, using a tip junction 13 that aligns each spine 11 in position can help in ensuring that the array of electrodes are not affected by ridges at the target tissue site.

In use, the internal support members 21 are embedded within shells of the spines 11. When the spines deflect between the collapsed and expanded profiles, the elbow regions 25 bend while the distal segments 24 and the proximal segments 26 remain substantially straight. During expansion of the electrode assembly 10, the spines 11 form angular configurations as shown in FIGS. 3B and 3C to reach the expanded profile of FIG. 3D.

In addition to, or as an alternative to structural variations in the inner support member 21, the inner support member 21 may use material variation along the length of the support member 21 to cause the desired deflection at the elbow regions 25. Furthermore, shape memory alloy such as Nitinol may be used to facilitate bending at the elbow region 25 and may also be adapted to bias the inner support member 21 toward the expanded profile when the force that is applied to collapse the electrode assembly 10 is removed.

Other embodiments that do not employ inner support members 21 embedded within the spines 11 are expressly contemplated. In those embodiments, the spines 11 may be modified so that deflectability is a direct result of the structural and/or material variation of the spines 11 themselves. In those embodiments, the spines 11 can have shapes and material make-up similar to those described above for the internal support members 21. For example, the spines 11 can have shapes similar to those of the support members 21 as depicted in FIGS. 4A-4D.

In yet another embodiment, the expansion and collapse of the electrode assembly 10 can be controlled without using an adjusting member 14. In one alternative design, no adjusting member is needed. Instead, the electrode assembly 10 is biased toward the expanded profile when the force that is applied to collapse the electrode assembly 10 is removed. This can be achieved, for instance, by using a shape memory material such as Nitinol for the spines 11. In another alternative design, an adjusting member may be embedded in at least one of the spines 11 or a pair of opposing spines 11 (in the same manner as the internal support member 21). The embedded adjusting member can be used to adjust the expansion and collapse of the electrode assembly 10, while optionally a shape memory material or the like may be used to bias the electrode assembly 10 toward the collapsed profile. Furthermore, the embedded adjusting member may optionally be used to tilt the electrode assembly 10 relative to the shaft 16.

Figure 6:
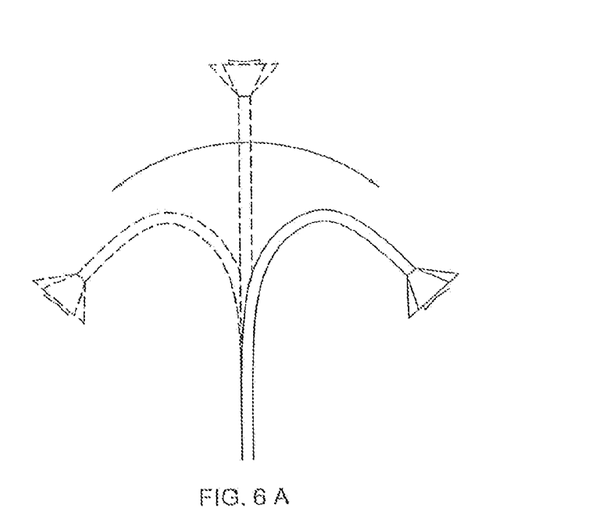
FIGS. 6A and 6B are side views of two catheter shafts showing different degrees of shaft deflection.

While the electrode assembly 10 has been discussed in detail above, the following relates to the directional control of the electrode assembly 10 as effected by tilting movement of the electrode assembly 10 relative to the shaft 16 as well as tilting of the shaft 16. As shown in FIG. 2A, the flat wire 15 is disposed within the shaft 16 for bi-directional deflection of the shaft 16. One of ordinary skill in the art will recognize that other types and shapes of wires can be used in place of, or in addition to, the flat wire 15 to effectuate the same unidirectional, bidirectional or multi-directional deflection. FIGS. 6A and 6B are side views of two catheter shafts showing different degrees of shaft deflection. FIG. 6A shows a larger degree of deflection than FIG. 6B.

Figure 7:
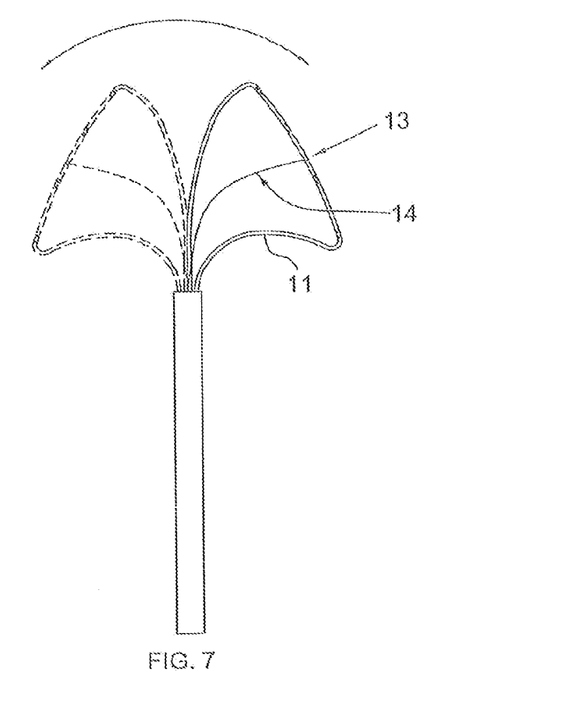
FIG. 7 is a side view of the distal region of a catheter shaft showing the tilting of the electrode assembly using an adjusting member attached to the tip junction.

In yet another embodiment, the adjusting member 14 can optionally be deflectable, much like the flat wire 15, or with the help of an additional flat wire (not shown) or guide wire (not shown). Referring to FIG. 7, by making the adjusting member 14 user-selectively deflectable, a user can tilt the electrode assembly 10 and control the degree and direction of the tilt by deflecting the adjusting member 14. In that case, the adjusting member 14 may be formed as a flat wire.

In still another embodiment, the flat wire 15 within the shaft 16 controls tilting of the shaft 16, while a deflectable adjusting member 14 controls tilting of the electrode assembly 10 relative to the shaft 16. This can be referred to as a dual distal deflection design, allowing the user to separately tilt the electrode assembly 10 (as shown in FIG. 7) and also tilt the shaft 16 in another direction (as shown in FIGS. 6A and 6B). This combination provides enhanced maneuverability and dexterity of the electrode assembly 10 of the basket catheter.

Figure 8A:
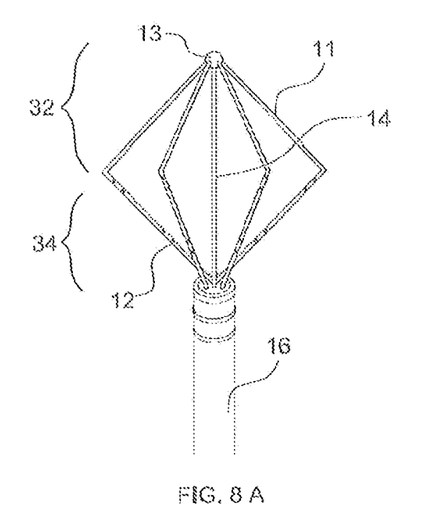
FIG. 8A is a perspective view of an electrode assembly having electrodes disposed between the elbows and the proximal ends of the spines according to another embodiment.
Figure 8B:
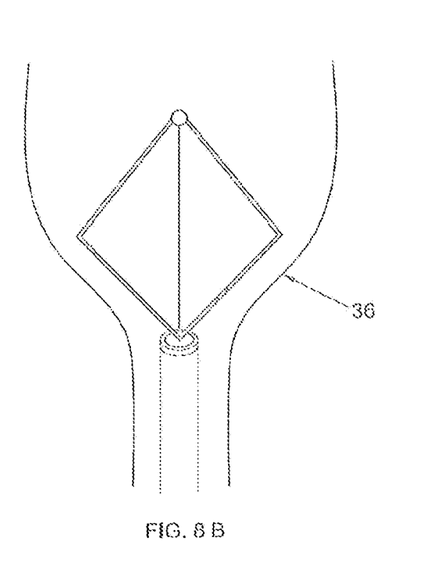
FIG. 8B illustrates the use of the electrode assembly of FIG. 8A in a body cavity such as for mapping or ablating the left atrium.

FIG. 8A is a perspective view of an electrode assembly having electrodes disposed in the proximal segments 34 between the elbows and the proximal ends of the spines 11 according to another embodiment. The distal segments 32 do not include any electrodes. As seen in FIG. 8B, the electrode assembly of FIG. 8A is inserted into a body cavity for mapping or ablating tissue. The electrode assembly is inserted in the collapsed state in the distal, direction via a body lumen into the target body cavity and changes into the expanded profile inside the target body cavity 36. In one example, the user then moves the electrode assembly in the proximal direction to make contacts between the electrodes 12 on the proximal segments 34 and the tissue surface of the target body cavity. This method is particularly effective to ablate the left atrium 36 of the heart.

Figure 9A:
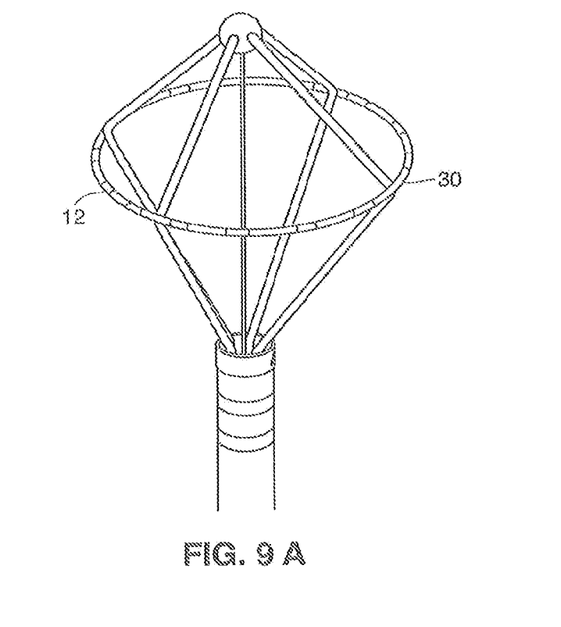
FIG. 9A is a perspective view of an electrode assembly having a transverse spine or link with electrodes according to another embodiment of the invention.

FIG. 9A is a perspective view of an electrode assembly having a collapsible transverse spine or link 30 with electrodes 12 according to another embodiment of the invention. The collapsible transverse spine 30 is connected to the elbows of the longitudinal spines and is disposed generally transverse to the longitudinal axis of the catheter. The transverse link 30 may include a shape memory material that biases the spines toward the expanded arrangement. When the electrode assembly is in the expanded profile, the transverse spine 30 forms a loop which may lie on a plane that is generally transverse to the longitudinal axis of the catheter shaft. While FIG. 9A shows a substantially circular loop, the transverse spine 30 may form other shapes in the expanded profile.

Figure 9B:
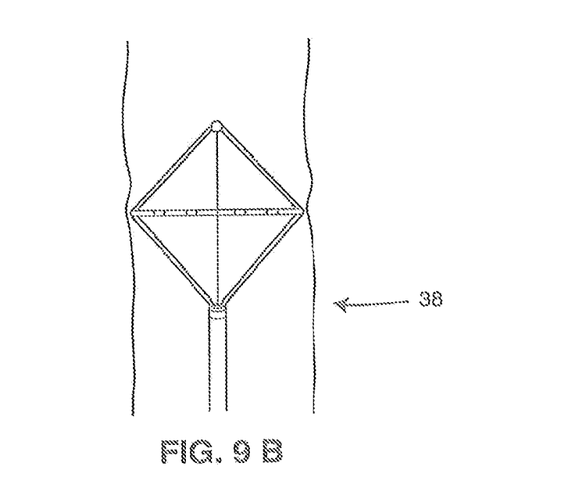
FIG. 9B illustrates the use of the electrode assembly of FIG. 9A in a body cavity such as for ablating the pulmonary vein.

As seen in FIG. 9B, the transverse spine 30 having the electrodes 12 may be particularly suitable for use in a body cavity such as for ablating the wall of a pulmonary vein 38. A contemplated method of ablation involves inserting a collapsed electrode assembly into the target body cavity, and expanding, the electrode assembly to allow the collapsible transverse spine 30 to make contact with surrounding tissue for ablation. In this case, the surrounding tissue is the wall of a pulmonary vein 38. In another embodiment, the longitudinal spines have ablation electrodes disposed at the elbows thereof, and there is no need for the transverse spine 30 with ablation electrodes.

The contemplated catheter and its component parts can be made of suitable materials known in the art of ablation catheters. Such materials include natural and synthetic polymers, various metals and metal alloys, naturally occurring materials, textile fibers, glass and ceramic materials, and all reasonable combinations thereof. The contemplated catheter and its component parts can be made in known sizes suitable for use in performing tissue ablation. In one contemplated embodiment, the shaft 16 has a diameter of about 6 to 8 femtometer.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that, all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
an elongated catheter body having a proximal end and a distal end, and at least one lumen therethrough in a longitudinal direction of the elongated catheter body;
a handle connected to the proximal end of the elongated catheter body, wherein the handle is configured to deflect the distal end of the elongated catheter body;
an electrode assembly at the distal end of the catheter body, the electrode assembly comprising a plurality of spines, each of the spines having a proximal end connected to the distal end of the catheter body and a distal end, the distal ends of the spines being connected at a tip junction, wherein each spine includes an elbow, wherein the spines include a plurality of electrodes; and
a tilting mechanism to tilt the electrode assembly with respect to the elongated catheter body;
wherein the electrode assembly is sized and configured to fit in a sheath in a collapsed arrangement and is configured to expand to an expanded arrangement with the elbows of the spines bending outwardly relative to the proximal and distal ends of the spines, the elbows of the spines moving radially outwardly from the collapsed arrangement to the expanded arrangement.

2. The catheter of claim 1, wherein the elbow of each spine has at least one discontinuity in stiffness resulting from at least one of a change in material, a change in cross-sectional arrangement, and a change in cross-sectional area.

3. The catheter of claim 1, wherein each spine has electrodes only between the elbow and the distal end thereof or only between the elbow and the proximal end thereof.

4. The catheter of claim 1, further comprising a bending mechanism to bend the elongated catheter body.

5. The catheter of claim 1, wherein the spines include mapping electrodes, and wherein the tip junction includes an ablation electrode.

6. The catheter of claim 1, wherein the spines include mapping electrodes, the electrodes in one spine being spaced differently from the electrodes in another spine.

7. The catheter of claim 1, wherein at least one of the spines includes a shape memory material that biases the spine toward the expanded arrangement.

8. The catheter of claim 1, wherein at least one spine has an ablation electrode disposed at the elbow thereof.

9. The catheter of claim 1, further comprising an adjusting, member which has a distal end connected to the tip junction and a proximal end which is movable in the longitudinal direction of the elongated catheter body, wherein movement of the adjusting member changes the shape of the electrode assembly.

10. The catheter of claim 1, wherein the tilting mechanism comprises a flat wire.

11. A catheter comprising:
   an elongated catheter body having a proximal end and a distal end, and at least one lumen therethrough in a longitudinal direction of the elongated catheter body;
   a handle connected to the proximal end of the elongated catheter body, wherein the handle is configured to deflect the distal end of the elongated catheter body; and
   an electrode assembly at the distal end of the catheter body, the electrode assembly comprising a plurality of spines, each of the spines having a proximal end connected to the distal end of the catheter body and a distal end, the distal ends of the spines being connected at a tip junction, wherein each spine includes an elbow having at least one discontinuity in stiffness at an intermediate position between the distal end and the proximal end thereof, wherein the spines include a plurality of electrodes; and
   a deflectable adjusting member which has as distal end connected to the tip junction and a proximal end which is movable in the longitudinal direction of the elongated catheter body;
   wherein movement of the deflectable adjusting member in the longitudinal direction of the catheter body changes the shape of the electrode assembly between a collapsed arrangement in which the electrode assembly is sized and configured to fit within a lumen of a sheath and different expanded arrangements with the elbows of the spines bending outwardly relative to the proximal and distal ends of the spines, the elbows of the spines moving radially outwardly from the collapsed arrangement to the expanded arrangement, and wherein the deflectable adjusting member is deflectable to tilt the electrode assembly with respect to the distal end of the elongated catheter body.

12. The catheter of claim 11, wherein the elbow of each spine has at least one discontinuity in stiffness resulting from at least one of a change in material, a change in cross-sectional arrangement, and a change in cross-sectional area.

13. The catheter of claim 11, wherein each spine has electrodes only between the elbow and the distal end thereof.

14. The catheter of claim 11, wherein the spines include mapping electrodes, the electrodes in one spine being spaced differently from the electrodes in another spine.

15. The catheter of claim 11, wherein at least one spine has an ablation electrode disposed at the elbow thereof.

* * * * *